United States Patent [19]

Kaiya

[11] Patent Number: 5,178,130
[45] Date of Patent: Jan. 12, 1993

[54] PARENT-AND-SON TYPE ENDOSCOPE SYSTEM FOR MAKING A SYNCHRONIZED FIELD SEQUENTIAL SYSTEM ILLUMINATION

[75] Inventor: Haruhiko Kaiya, Hachioji, Japan

[73] Assignee: Olympus Optical Co., Ltd., Tokyo, Japan

[21] Appl. No.: 647,622

[22] Filed: Jan. 29, 1991

[30] Foreign Application Priority Data

Apr. 4, 1990 [JP] Japan ................................ 2-91834

[51] Int. Cl.[5] ..................... A61B 1/06; H04N 7/18
[52] U.S. Cl. ...................................... 128/6; 358/98
[58] Field of Search ................ 128/6, 4, 634; 358/98, 358/42; 606/46

[56] References Cited

U.S. PATENT DOCUMENTS

| 4,601,284 | 7/1986 | Arakawa et al. | 128/6 |
| 4,827,909 | 5/1989 | Kato et al. | 128/6 |
| 4,870,488 | 9/1989 | Ikuno et al. | 358/98 |
| 4,885,635 | 12/1989 | Kimura et al. | 358/98 |

FOREIGN PATENT DOCUMENTS 61-234834 10/1986 Japan .

Primary Examiner—Vincent Millin
Assistant Examiner—John P. Leubecker
Attorney, Agent, or Firm—Armstrong & Kubovcik

[57] ABSTRACT

An endoscope system wherein a first electronic endoscope apparatus and second electronic endoscope apparatus are used as combined characterized in that a field sequential illuminating system forming a first electronic endoscope apparatus and a field sequential illuminating system forming a second electronic endoscope apparatus are synchronized by a synchronizing signal to make an illumination so that neither apparatus may produce such deterioration of the picture quality as the break of the color balance and a smear or the like.

14 Claims, 9 Drawing Sheets

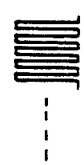
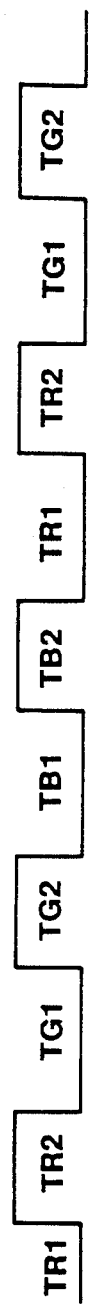
FIG.5 a CK
FIG.5 b S1
FIG.5 c PERIOD OF DRa
FIG.5 d S2
FIG.5 e VD OF SYNC
FIG.5 f SA(SB)
FIG.5 g SA'(SB')

FIG. 6
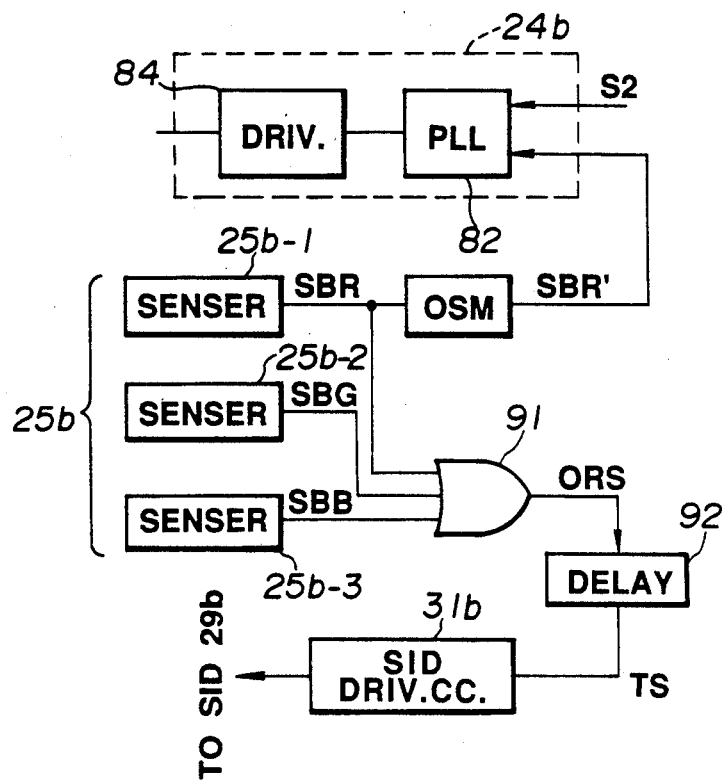
| FIG.7a | S1 |  |
| --- | --- | --- |
| FIG.7b | DRa |  |
| FIG.7c | ORS | 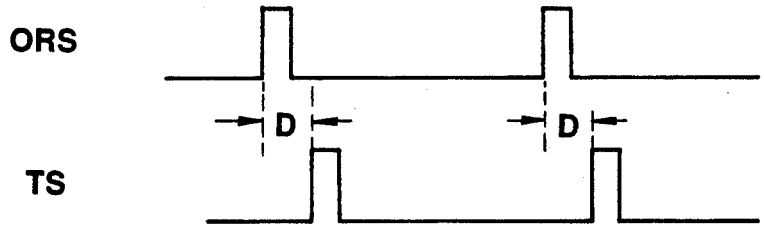 |
| FIG.7d | TS |  |
| FIG.7e | DRb |  |

PARENT-AND-SON TYPE ENDOSCOPE SYSTEM FOR MAKING A SYNCHRONIZED FIELD SEQUENTIAL SYSTEM ILLUMINATION

BACKGROUND OF THE INVENTION

Field of the Invention and Related Art Statement

This invention relates to a parent-and-son type endoscope system for making an observation with a first endoscope and a second endoscope used as combined as by being inserted into a channel of the first endoscope.

Recently, endoscopes have come to be extensively used not only in the medical field but also in the industrial field.

Such a endoscope is provided with a channel insertable through a treating instrument so that a therapeutic treatment may be made with the treating instrument.

There is a case that an endoscope having an insertable section of a fine diameter is inserted through this channel and is used as a parent-and-son type endoscope. A parent-and-son type endoscope system using parent and son endoscopes is disclosed in the publication of Japanese Patent Application Laid Open No. 234834/1986.

In this prior art example, it is disclosed that an image of a TV camera externally fitted scope with a TV camera fitted to a parent side video scope or fiber scope and an image of a son side video scope or TV camera externally fitted scope are displayed in one TV monitor by an image mixer.

In this prior art example, in case a simultaneous type video scope or TV camera whereby an imaging is made by an imaging means provided with a color separating filter under an illumination of a white light is used, no problem will be produced but, in case a field sequential type video scope or TV camera whereby a sequential imaging is made under respective illuminating lights of different wavelength ranges is used, unless the R,G,B lights (field sequential lights) on the parent side and son side are synchronized, there will be problems that the colors will not be able to be reproduced, Further a light in another illuminating period will enter a solid state imaging device forming the imaging means in one blanking period, therefore a smear or blooming will be generated and the picture quality will deteriorate.

That is to say, in the field sequential type imaging system, an object to be imaged is illuminated with a field sequential light by a field sequential type illuminating means and the light reflected from the object is made to form an image on the imaging surface of such solid state imaging device as a CCD having no color separating filter through an objective optical system. A signal accumulated as a charge or the like photoelectrically converted by applying a driving signal to the solid state imaging device is read out in the next light intercepting period and is once memorized as a component image in the respective memories corresponding to the respective field sequential lights. When a plurality of component images corresponding to one color image are memorized, they will be simultaneously read out to produce a color video signal.

Therefore, unless the illuminating states of two field sequential type video scopes are substantially synchronized with each other, the colors will not be able to be reproduced. For example, when the field sequential light of one video scope apparatus is red but the field sequential light of the other video scope apparatus is green, the component image obtained by these added lights will be processed as red and green component images in the respective apparatus. In this case, there is a problem that the signal level of the red component image will become large in one video scope apparatus. That is, the color reproductivity will be obstructed. This problem will be produced even if not only a line transfer type but also interline transfer type and frame transfer type of solid state imaging devices are used.

Also, when one video scope apparatus is in an illuminating state (period) but the other video scope apparatus is in a signal reading state (period), in this reading state, a charge transfer will be made on the imaging surface. Therefore in the case of a solid state imaging device in which the imaging section and transfer section are of a common line transfer type and are adapted to be made small, a photoelectrically converted signal caused by the illuminating light of one apparatus will be mixed with a signal being transferred and will produce a smear. Also, due to the mixed signal, the signal level will rise and will overflow the periphery to cause a blooming.

These defects will be generated not only in the parent-and-son type endoscope system but also in the case of using two endoscopes as combined.

OBJECTS AND SUMMARY OF THE INVENTION

An object of the present invention is to provide a parent-and-son type endoscope system whereby an endoscope image high in the picture quality can be obtained without deteriorating the color reproductivity.

Another object of the present invention is to provide a parent-and-son type electronic endoscope system whereby further no smear and blooming are generated.

Further another object of the present invention is to provide a composite type electronic endoscope system convenient to use.

In the present invention, in an endoscope system in which a first electronic type endoscope apparatus and a second electronic type endoscope apparatus are used as combined, a field sequential illuminating system forming the first electronic type endoscope apparatus and a field sequential illuminating system forming the second electronic type endoscope apparatus are made to make a field sequential illumination synchronized by a synchronizing signal from a synchronization controlling means so that such deterioration of the picture quality as a failure of the color balance and a cause of producing a smear and the like may be excluded.

BRIEF DESCRIPTION OF THE DRAWINGS

FIGS. 1 to 5 relate to the first embodiment of the present invention.

FIG. 1 is a block diagram showing the whole formation of the first embodiment.

FIG. 2 is an appearance view of the first embodiment.

FIG. 3 is a perspective view showing a part of a light source apparatus.

FIG. 4 is a block diagram showing the formation of a signal processing circuit or the like.

FIG. 5 is a timing chart for explaining the operation of the first embodiment.

FIGS. 6 and 7 relate to a first modification of the first embodiment of the present invention.

FIG. 6 is a block diagram of an essential part in the first modification of the first embodiment.

FIG. 7 is a timing chart for explaining the operation in FIG. 6.

FIG. 9 is a block diagram showing the whole formation of the second embodiment.

FIG. 10 is an appearance view of the second embodiment.

DETAILED DESCRIPTION OF THE PREFERRED EMBODIMENTS

Figure 1:
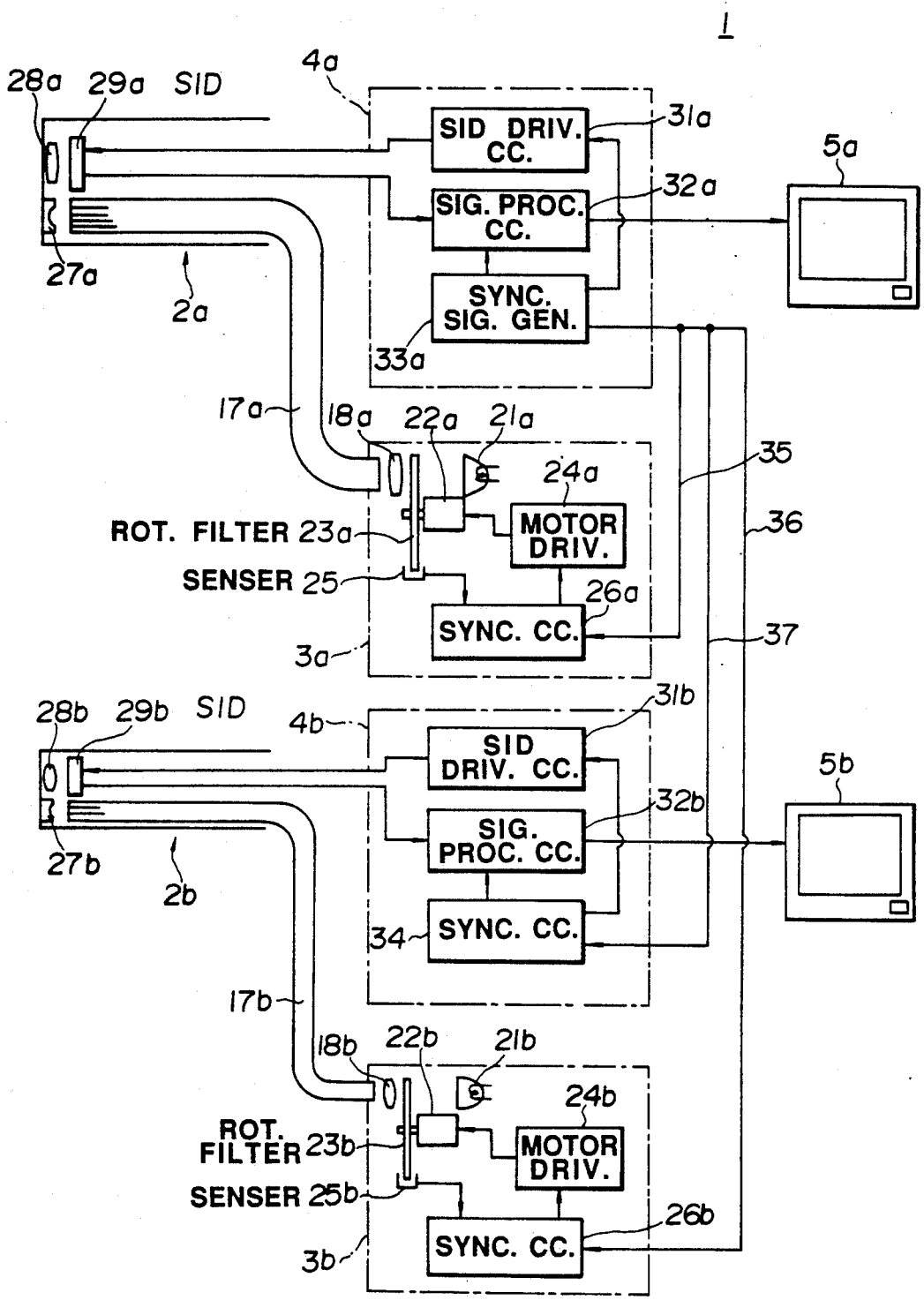
Figure 2:
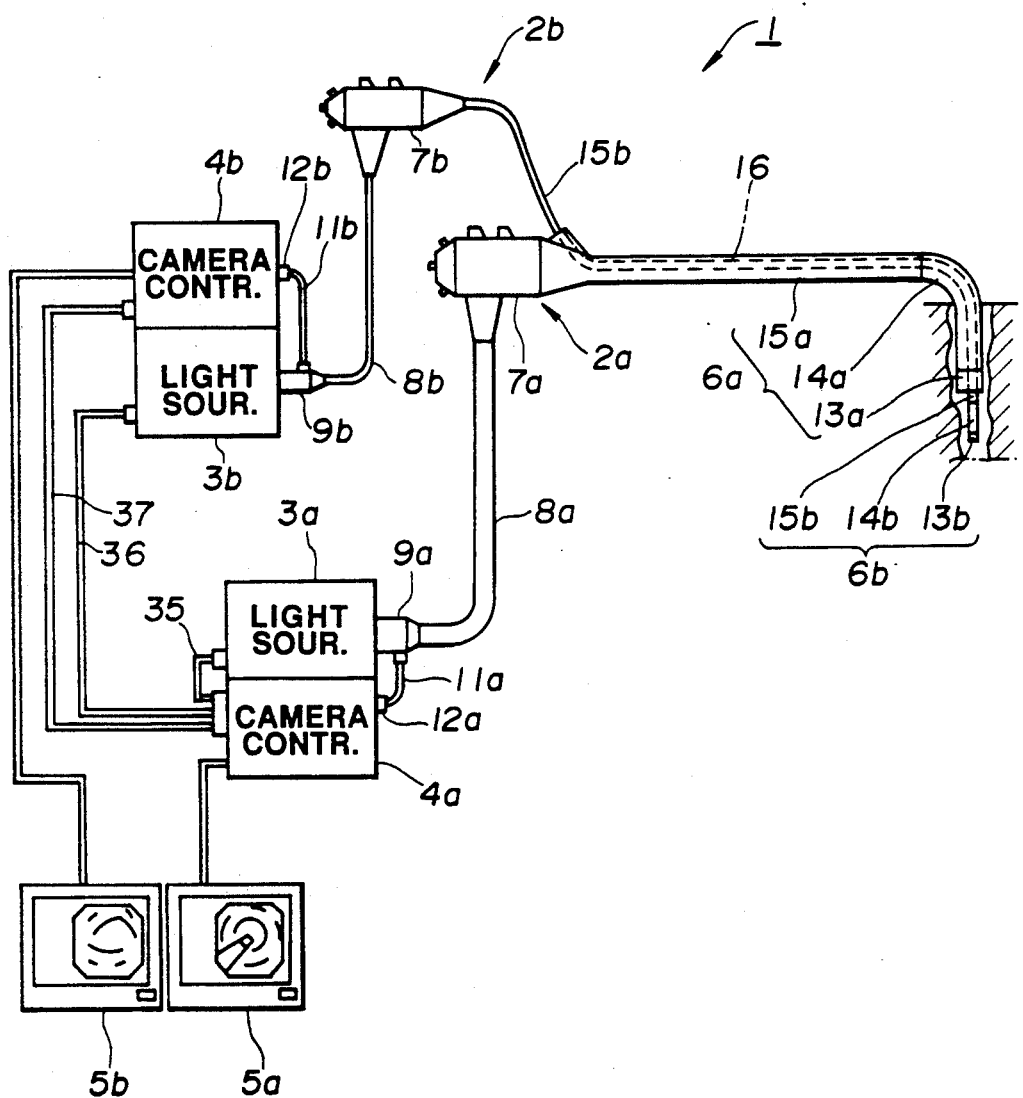

As shown in FIGS. 1 and 2, the parent-and-son type endoscope system 1 of the first embodiment comprises a field sequential type parent side video scope 2a, a field sequential type son side video scope 2b to be used together with this parent side video scope 2a, light source apparatus 3a and 3b connected respectively with these parent side and son side video scopes 2a and 2b and feeding field sequential type illuminating lights, camera controllers 4a and 4b processing signals for the respective imaging means of the above mentioned parent side and son side video scopes 2a and 2b and monitors 5a and 5b connected respectively with the camera controllers 4a and 4b and displaying endoscope images.

The above mentioned parent side and son side video scopes 2a and 2b comprise respectively elongate insertable sections 6a and 6b, thick operating sections 7a and 7b connected respectively to the insertable sections 6a and 6b at the rear ends and universal cables 8a and 8b extended respectively out of the sides of the operating sections 7a and 7b. The universal cables 8a and 8b are provided at the tips respectively with connectors 9a and 9b connectable respectively to the light sources 3a and 3b.

Connecting cables 11a and 11b are extended respectively out of the connectors 9a and 9b and are provided respectively with signal connectors 12a and 12b connectable respectively with the camera controllers 4a and 4b.

The above mentioned insertable section 6i (i=a or b) comprises a tip section 13i, a curvable section formed at the rear end of this tip section 13i and a long flexible (soft) section extending from the rear end of the curvable section 14i to the front end of the operating section 7i.

As shown in FIG. 2, the parent side video scope 2a is provided with a channel 16 communicating with an opening to be an inserting port near the base end of the operating section 7a and an opening of the tip section 13a so that the insertable section 6b of the son side video scope 2b may be inserted through this channel 16. That is to say, the inside diameter of the channel 16 is made larger than the outside diameter of the insertable section 6b of the son side video scope 2b.

As shown in FIG. 1, a light guide (fiber) 17i transmitting an illuminating light is inserted through the insertable section 6i of each video scope 2i and is further inserted through the universal cable 8i from the operating section 7i. When the connector 9i is connected to the light source apparatus 3i, field sequential lights, for example, R, G, B lights will be fed from the light source apparatus 3i.

Figure 3:
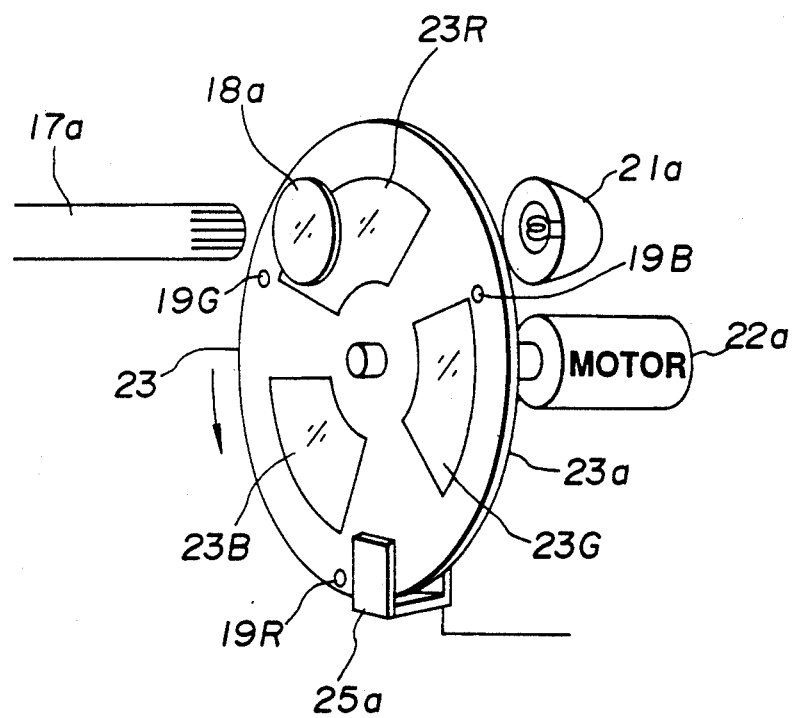

As shown in FIG. 3, when a white light of a lamp 21i is radiated to a rotary (color) filter 23i rotated and driven by a motor 22i, the white light will pass sequentially through R, G and B transmitting filters 23R, 23G and 23B fitted to fan-shaped windows formed in the peripheral direction of a light intercepting disc to be made R, G and B sequential lights which will be condensed by a lens 18i and will be radiated to the light guide 17i on one end surface.

The above mentioned motor 22i is rotated and driven by a motor driving signal from a motor driving circuit 24i. A position sensor 25i is arranged in a proper position on the outer periphery of the rotary filter 23i so that, by this position sensor 25i, the rotating position of the rotary filter 23i, that is, the timing just after the end of the period when the R, G and B transmitting filters 23R, 23G and 23B are in the illuminating light path may be detected by detecting the positions of holes 19R, 19G and 19B and the detecting signal, for example, of the hole 19R (that is, at the time of the end of a red illuminating period) may be input into a synchronizing circuit 26i. The output signal of this synchronizing circuit 26i is input into a motor driving circuit 24i so that, by this output signal, the timing of the motor driving signal driving the motor 22i may be controlled.

The illuminating light transmitted through the above mentioned light guide 17i is emitted forward further through a concave lens 27i from the tip surface.

The object illuminated by this emitted illuminating light is imaged on a solid state imaging device (abbreviated as SID hereinafter) arranged in the image forming plane by an objective lens 28i provided in the tip section 13i and the image is photoelectrically converted. For the SID 29i of this embodiment is used a line transfer type CCD for which the imaging section and transferring section are common and which is adapted to be made small.

An SID driving signal is applied to the SID 29i forming the imaging means from an SID driving circuit 31i within the camera controller 4i and a photoelectrically converted signal charge is read out as an image signal. This read image signal is input into a signal processing circuit 32i and is processed to be converted to a standard video signal which is output to a monitor 5i to display the object image.

A synchronizing signal generating circuit 33a generating a synchronizing signal is provided within the camera controller 4a. This synchronizing signal is transmitted to the signal processing circuit 32a and SID driving circuit 31a to synchronize the timing of driving (reading) the SID 29a and the timing of processing the read image signal with each other.

On the other hand, a synchronizing circuit 34 outputting a synchronizing signal synchronized with an input synchronizing signal is provided within the other (son side) camera controller 4b and the synchronizing signal output from this synchronizing circuit 34 is transmitted to the signal processing circuit 32b and SID driving circuit 31b to synchronize the timing of driving the SID 29b and the timing of processing the signal with each other.

The synchronizing signal from the synchronizing signal generating circuit 33a of the above mentioned camera controller 4a is transmitted to the synchronizing circuit 26a within the light source apparatus 3a through a synchronizing signal cable 35. This synchronizing circuit 26a controls the motor driving circuit 24a so that this input synchronizing signal and the output signal of the sensor 25a may be synchronized with each other. Thus, by the synchronizing signal from the synchronizing signal generating circuit 33a, the timings of the reading signal (driving signal) to the SID 29a, the read image signal and the illuminating period of R, G, B lights (R, G, B sequential lights) on the light source apparatus 3a side may be synchronized. For example, at the timing when the illuminating period of the R light ends, the driving circuit 31a will output an SID driving signal to the SID 29a and the image signal output from the SID 29a will be input into the signal processing circuit 32a in which the image signal will be stored in the frame memory as synchronized with the synchronizing signal. The timing when the stored image signal is read out of the frame memory and a standard video signal is produced will be synchronized with the synchronizing signal.

The synchronizing signal of the above mentioned synchronizing signal generating circuit 33a is input into the synchronizing circuit 26b within the son side light source apparatus 3b and the synchronizing circuit 34 within the son side camera controller 4b respectively through synchronizing signal cables 36 and 37.

That is to say, the timing of the illuminating period (light intercepting period) of the R, G, B sequential lights of the son side light source apparatus 3b is synchronized with this synchronizing signal by the synchronizing signal from the synchronizing signal generating circuit 33a within the parent side camera controller 4a. Also, the synchronization of the timing of the SID driving signal output from the SID driving circuit 31b within the son side camera controller 4b and the timing of processing the read image signal is synchronized with this synchronizing signal.

Thus, it is a feature of this first embodiment that, by the synchronizing signal within the parent side camera controller 4a, the timing of the R, G, B sequential lights by the parent side light source apparatus 3a and son side light source appartus 3b is synchronized and the SID driving system and signal processing system within the parent side camera controller 4a and the SID driving system and signal processing system within the son side camera controller 4b are synchronized.

Figure 4:
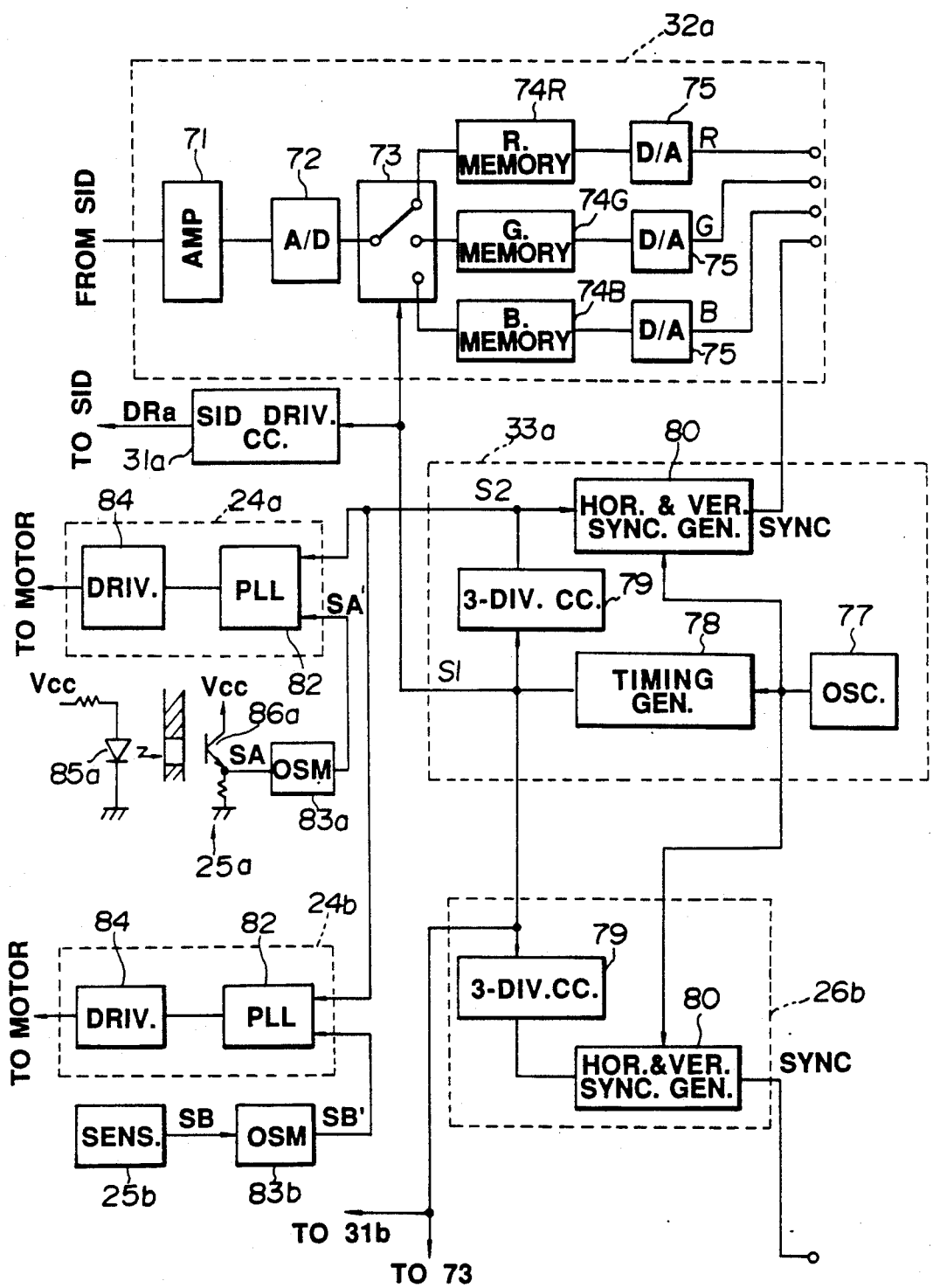

The formations of the above mentioned signal processing circuit 32a and synchronizing signal generating circuit 33a are shown in FIG. 4. The signal processing circuits 32a and 32b are of the same formation and the light source apparatus 3a and 3b are also of the same formation.

For example, the signal output from the SID 29 is input and amplified in an amplifier 71 and is then converted to a digital signal by an A/D converter 72. This digital signal is written sequentially into R, G, B memories 74R, 74G and 74B. The signal imaged, for example, under a red illuminating light is written into the R memory 74R. When a component image by one color frame is written in, signals in these memories 74R, 74G and 74B will be simultaneously read out and will be converted to analogue signals, for example, three primary color signals R, G and B respectively by D/A converters 75. These three primary color signals R, G and B will be output to the color monitor 5a together with a horizontal and vertical synchronizing signal SYNC from the synchronizing signal generating circuit 33a.

In the above mentioned synchronizing signal generating circuit 33a, a clock CK oscillated by an oscillator 77 and shown in FIG. 5a is output to a timing generator 78 formed of a frequency dividing circuit or the like. This timing generator 78 produces a first synchronizing signal S1 (See FIG. 5b) of a frequency three times as high as, for example, of a vertical synchronizing signal VD (See FIG. 5e) and outputs it to a 3-frequency dividing circuit 79. The pulse width of this signal S1 is set so as not to exceed the light intercepting period by the rotary filter 23a.

This synchronizing signal S1 is output to the SID driving circuit 31a to control the timing so that, when this signal S1 is "H", the SID driving circuit 31a may output a driving signal DRa to the SID.29a (See FIG. 5c) and is output to a multiplexer 73 to control switching to write the signal output from the SID 29a (by applying the above mentioned driving signal DR) sequentially into the R, G and B memories 74R, 74G and 74B.

The above mentioned 3-frequency dividing circuit 79 divides the frequency of the synchronizing signal S1 into three divisions to produce a second synchronizing signal S2 shown in FIG. 5d and outputs the S2 to a horizontal and vertical synchronization generating circuit 80. The clock CK from the oscillator 77 is also input into this horizontal and vertical synchronization generating circuit 80 and a horizontal and vertical synchronizing signal SYNC is produced from the signal S2 and clock CK. In FIG. 5e, for the brevity, only a vertical synchronizing signal VD in this horizontal and vertical synchronizing signal SYNC is shown.

The second synchronizing signal S2 output from the above mentioned 3-frequency dividing circuit 79 is input into a PLL circuit 82 forming the motor driving circuit 31a within the light source apparatus 3a. An output SAR from the sensor 25a is made a signal SAR' adjusted to be of the same pulse width as of the second synchronizing signal S2 by a one shot multivibrator (abbreviated as OSM hereinafter) 83a and is input into this PLL circuit 82.

The above mentioned sensor 25a is formed of a photointerrupter comprising, for example, an LED 85a and a phototransistor 86a arranged as opposed to this LED 85a with the rotary filter 23a interposed between them.

The above mentioned PLL circuit 82 will be of an output of a large level when the phase of a detecting signal SAR' corresponding to the actual rotating speed of the motor advances with respect to the second synchronizing signal S2 to be a reference but will be of an output of a small level when the phase delays. The output of this PLL circuit 82 is output to the motor 22a through a driving circuit 84 and the rotating speed and phase of the motor 22a are controlled so that the phase of the detecting signal SAR' may coincide with the phase of the second synchronizing signal S2. Therefore, as shown in FIGS. 5g and 5d, the rotation of the motor 22a is controlled to keep the phase of the detecting signal SAR' coinciding with the phase of the second synchronizing signal S2.

The above mentioned first synchronizing signal S1 and clock CK are input respectively into the horizontal and vertical synchronization generating circuit 80 forming the son side synchronizing circuit 26 and into the 3-frequency dividing circuit 79. The second synchronizing signal S2 is input into (the PLL circuit 82 forming) the son side motor driving circuit 31b. The output SBR of the sensor 25b is made a detecting signal SBR' through the OSM 83b and is input into this motor driving circuit 31b.

The operations of the son side synchronizing circuit 26b and motor driving circuit 31b are the same as on the parent side. (For example, the output SBR of the sensor 25b is of the same phase as of the output SAR of the sensor 25a and the detecting signal SB' is also of the same phase as of the detecting signal SA'.)

By the way, the respective filters 23R, 23G and 23B in the rotary filters 23a and 23b are respectively equal in the lengths in the peripheral direction and are fitted at regular intervals. Therefore, in FIG. 5b, the first "L" period is a red ilulminating period TR1 and the next "H" period is a light intercepting period TR2 in which an SID driving signal is output in the SID's 29a and 29b. For example, the output signal of the SID 29a is input respectively into the signal processing circuits 32a and 32b, is amplified and A/D converted and is then memorized in an R memory 74R through a multplexer 73. The output signal of the SID 29b is also processed the same.

The next "H" period is a light intercepting period TG2 in which an SID driving signal is output in the SID's 29a and 29b. In this case, the output signal of the SID 29a will be memorized in a G memory 74G.

The next "L" period is a blue illuminating period TB1 and the next "H" period is a light intercepting period TB2 in which an SID driving signal is output in the SID's 29a and 29b. In this case, the output signal of the SID 29a will be memorized in a B memory 74B. The signals in these R, G and B memories 74R, 74G and 74B are simultaneously read out as synchronized with a vertical synchronizing signal VD and are displayed in the color monitor 5a. Those on the son side are also processed as synchronized with those on the parent side and are displayed in the color monitor 5b.

Now, the parent side video scope 2a has the SID 29a of a comparatively large number of pixels built-in in the tip section. It is an SID, for example, of about 50,000 to 100,000 pixels.

On the other hand, the son side video scope 2b has the SID 29b of a comparatively small number of pixels, for example, about 10,000 to 20,000 pixels built-in.

According to this first embodiment, by the synchronizing signal from the parent side camera controller 4a, the parent side and son side illuminating systems and signal processing systems (including the driving systems) are to be all synchronized. The case that, while one side is outputting an SID driving signal, the other is illuminating, that is, the case that such matter deteriorating the picture quality as a smear or blooming occurs can be prevented. The case that, for example, one side is illuminating with an R light but the other side is illuminating with a G light so that the color balance may be broken and the color reproductivity may deteriorate can be also prevented. Thus, the cause of deteriorating the picture quality can be excluded.

According to this first embodiment, there is an advantage that, in case the parent side video scope 2a is used as an endoscope for large intestines, the son side video scope 2b will be adapted to be used as a guide scope.

In this case, if the son side video scope 2b is provided in the tip section 13b with a balloon, it will be easy to insert the tip section 13b into the large intestine.

In case the parent side video scope 2a is used as an endoscope of a comparatively wide visual field angle for routine inspections, the son side video scope 2b will be adapted to be used as an endoscope of a narrow visual field angle for magnified observation. Then, a magnified observation will be able to be made without the necessity to provide the tip section 13a with a zoom lens and the pain given to the patient by the larger diameter of the tip section by the zoom lens mechanism which must be larger will be able to be dissolved.

Further, if the observation with the son side video scope 2b is made with the illumination on the parent side video scope 2a side, the son side light guide 17b will be able to be made unnecessary and therefore the son side video scope 2b will be able to be made smaller in the diameter. Thereby, the inside diameter of the channel 16 of the parent side video scope 2a may be small and therefore the outside diameters of the tip section 13a, curvable section 14a and soft section 15a can be made smaller. Further, as the son side light source apparatus 3b becomes unnecessary, the apparatus 1 or system can be formed cheaply. Further, if the curvable section 14b of the son side video scope 2b is not provided, the tip section 13b and soft section 15b of the son side video scope 2b will be able to be made smaller in the diameters and therefore the parent side video scope 2a will be also able to be made smaller in the diameter.

Now, the SID 29b of the above mentioned son side video scope 2b is considerably smaller in the number of pixels (for example, 1/several) than the SID 29a of the parent side video scope 2a and therefore, in case a driving signal of the same frequency is used, the required reading period may be considerably shorter than in the SID 29a.

Therefore, in the SID 29a, signals of many pixels must be read out by using the time from the beginning near to the end of the light intercepting period but, in the SID 29a, the timing of starting reading may be considerably free. Therefore, as shown, for example, in FIG. 6, a timing controlling signal TS is produced by delaying by the time D with a delaying device 92 an OR output ORS obtained by passing through an OR gate 91 the respective outputs SBR, SBG and SBB of sensors 25b-1, 25b-2 and 25b-3 detecting the respective light intercepting periods of red, green and blue and may be output to the SID driving circuit 31b. Here, the delaying time D can be set to be substantially 0 to 4/5, for example, of the light intercepting period (substantially equal to the period required to read out the number of pixels of the SID 29a).

The operation of this modification is shown in FIG. 7. An SID driving signal DRa is output as substantially synchronized with "H" of a synchronizing signal SI shown in FIG. 7a. On the other hand, the OR output ORS of the sensors 25b-1, 25b-2 and 25b-3 is as in FIG. 7c. When passed through the delaying device 92, this OR output ORS will become a timing controlling signal TS delayed by the delaying time D from the OR output ORS as shown in FIG. 7d. At the timing when this timing controlling signal TS becomes "H", the SID 29b will output an SID driving signal DRb as shown in FIG. 7e.

Figure 8:
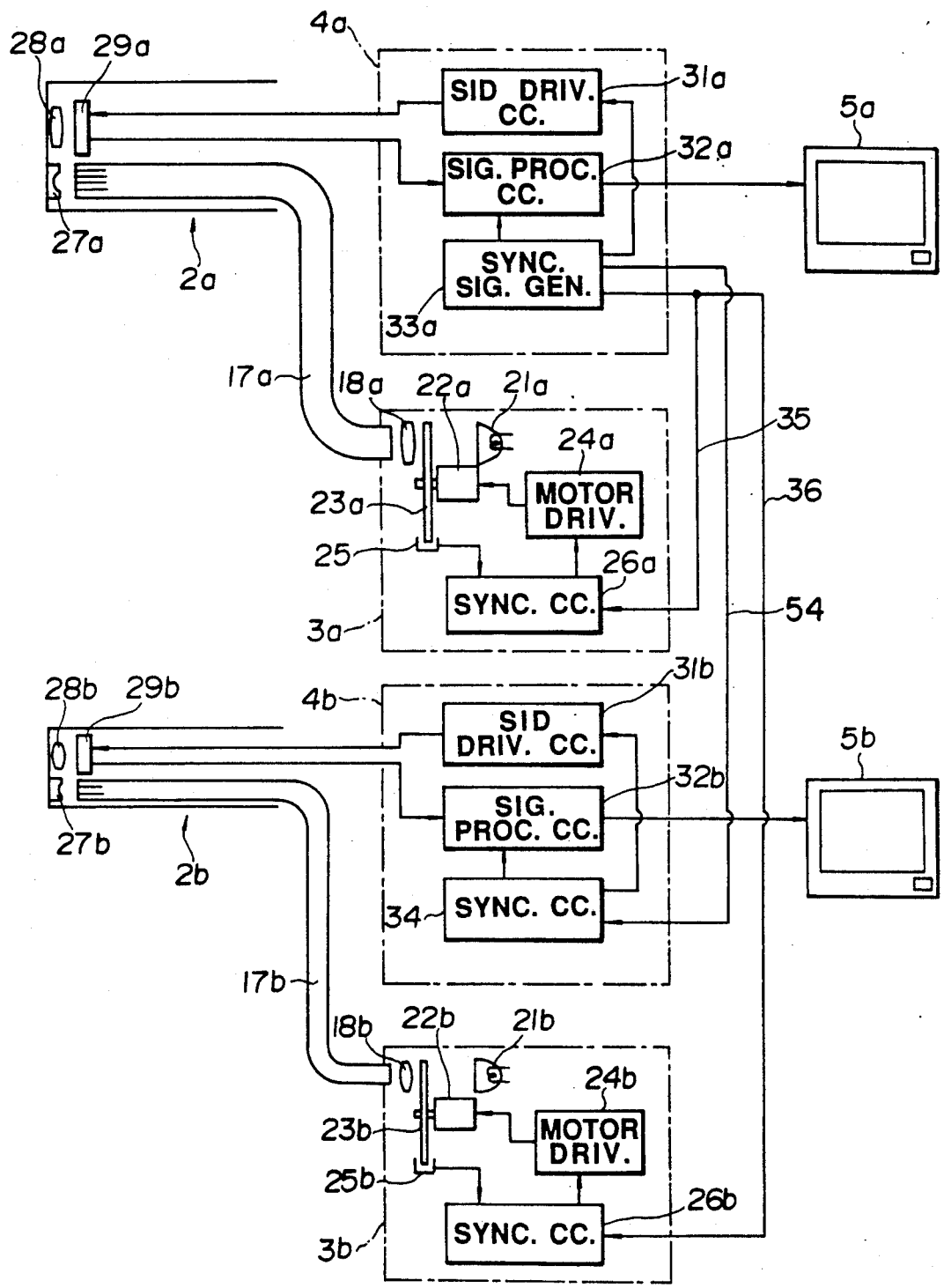
FIG. 8 is a block diagram showing a second modification of the first embodiment.

FIG. 8 shows a second modification of the first embodiment.

In the first embodiment, from the parent side camera controller 4a, the same synchronizing signal is output to the parent side light source apparatus 3a, son side light source apparatus 3b and son side camera controller 4b respectively through cables 35, 36 and 37 but, in this modification, the same synchronizing signal is transmitted to the parent side and son side light source apparatus 3a and 3b through the cables 35 and 36 and a synchronizing signal synchronized with this synchronizing signal is transmitted to the son side camera controller 4b through a cable 54.

The others are of the same formations as of the first embodiment and the operations and effects are the same.

Figure 9:
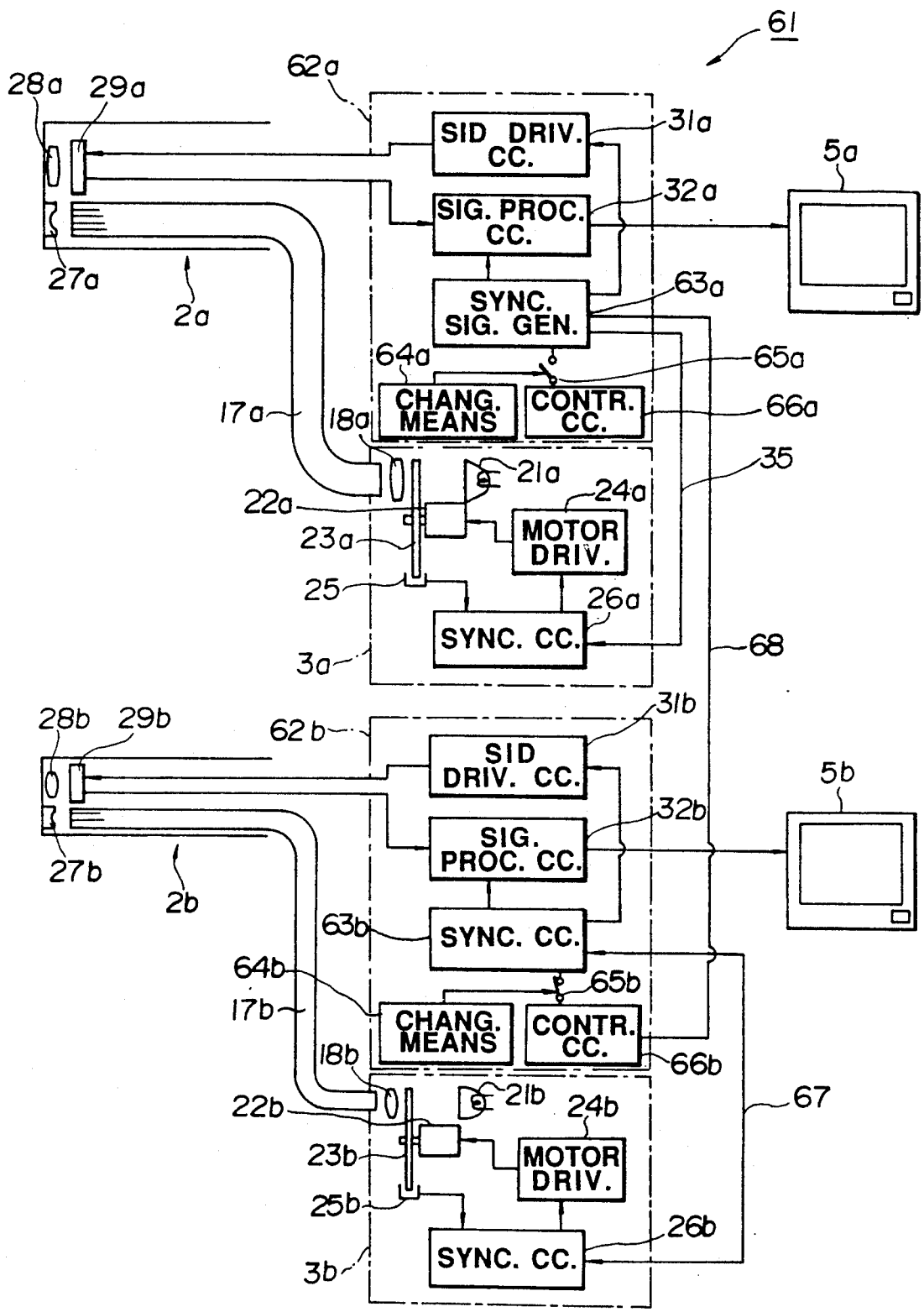
FIGS. 9 and 10 relate to the second embodiment of the present invention.
Figure 10:
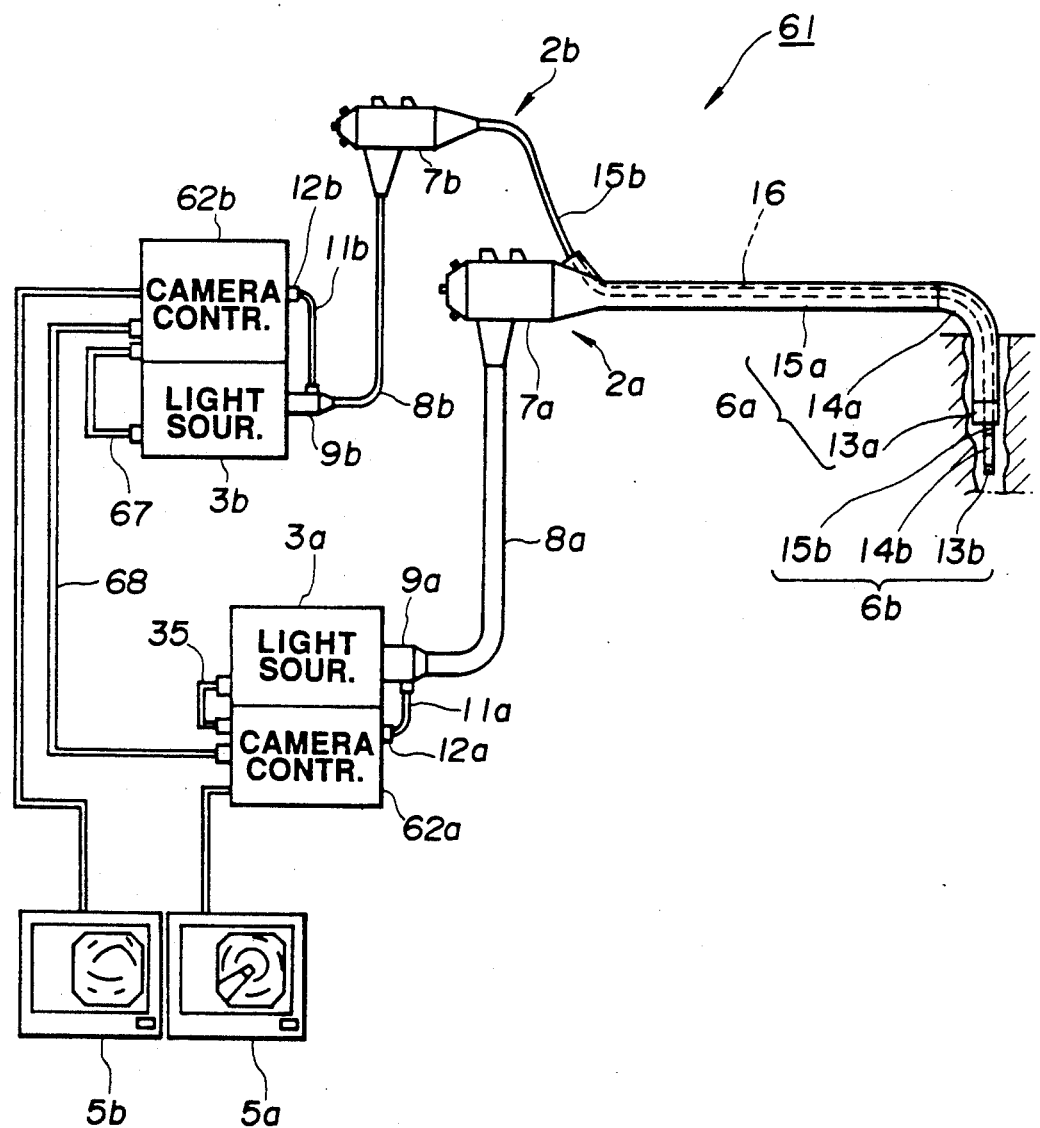

FIGS. 9 and 10 show an endoscope apparatus 61 of the second embodiment of the present invention.

In this second embodiment are used camera controllers 62a and 62b different partly in the formations from the parent side and son side camera controllers 4a and 4b in the first embodiment.

Each camera controller 62i has a synchronizing signal generating circuit 63i outputting synchronizing signals respectively to the SID driving circuit 31i and signal processing circuit 32i. The above mentioned synchronizing signal generating circuit 63i is connected with a switching means 64i for switching the internal synchronization and external synchronization with each other and a switch 65i is switched on/off by this switching means 64i. This switch 65i is connected also with a controlling circuit 66i so that, in case the switch 65i is connected with the controlling circuit 66i (in case the external synchronization is selected), the synchronizing signal generating circuit 63i will output a synchronizing signal synchronized with an external synchronizing signal input into a controlling circuit 66i and, in case the switch 65 is switched off (in case the internal synchronization is selected), the synchronizing signal generating circuit 63i will output an internal synchronizing signal (formed, for example, of a PLL or the like).

In this embodiment, the respective synchronizing signal generating circuits 63i output synchronizing signals synchronizing the timings of the operations of the signal processing systems (including the driving systems of the SID's) and illuminating systems respectively to the synchronizing circuits 26i of the light source apparatus 3i respectively through the cables 35 and 67. The synchronizing signal generating circuit 63a transmits the synchronizing signal from the synchronizing signal output end to the (external) synchronizing signal input end of the control circuit 66b of the son side camera controller 62b through the cable 68. The switch 65b is switched on and the synchronizing signal generating circuit 63b within the son side camera controller 62b outputs the synchronizing signal locked to the external synchronizing signal input through the control circuit 66b to the SID driving circuit 31b, signal processing circuit 32b and the synchronizing circuit 26b of the light source apparatus 3b.

The other formations are the same as in the first embodiment and are represented by the same reference numerals.

The operation and effects of this second embodiment are substantially the same as in the first embodiment.

Further, this embodiment has an advantage that, in case it is set by the switching means 64b to be internally synchronized, this embodiment will be able to be used as an ordinary endoscope apparatus formed of respectively one video scope 2i, light source apparatus 3i, camera controller 62i and monitor 5i.

By the way, in this second embodiment, the internal synchronization and external synchronization are switched over to each other by a manual switching means 64i but may be by an automatic switching system by sensing whether the synchronizing signal cable 68 is connected to the synchronizing signal input end of the control circuit 66b or not.

By the way, at least one video scope 2i can be formed of a television camera externally fitted scope (which is also an endoscope provided with an imaging means of the present invention) which is a fiber scope fitted with a field sequential type television camera.

By the way, for example, a video signal by the son side video scope 2b may be superimposed on a video signal by the parent side video scope 2a so that two images may be simultaneously displayed on one monitor 5a picture. (In this case, the timing for the synchronizing signal of one video signal period may be delayed in mixing.)

The present invention can be applied not only to an electronic endoscope system used as a parent and son but also to an electronic endoscope system used as combined.

As described above, according to the present invention, a plurality of field sequential illuminating systems used in combination of at least the parent side and son side are synchronized and therefore the reduction of the color reproductivity by the difference of colors of the illuminating lights and the deterioration of the picture quality by a smear and the like can be effectively prevented.

What is claimed is:

1. An endoscope system comprising:
    a first electronic endoscope comprising an elongate insertable section, a first light guide inserted through said insertable section, transmitting an illuminating light fed on one end surface and emitting the illuminating light from the other end surface, a first objective optical system provided on the tip side of said insertable section and a first solid state imaging device photoelectrically converting an optical image based on said first objective optical system;
    a second electronic endoscope comprising an elongate insertable section, a second light guide inserted through said insertable section, transmitting an illuminating light fed on one end surface and emitting the illuminating light from the other end surface, a second objective optical system provided on the tip side of said insertable section and a second solid state imaging device photoelectrically converting an optical image based on said second objective optical system;
    first and second light source apparatus respectively sequentially feeding as a first and second field sequential illuminating lights a plurality of illuminating lights different in the wavelength range to the end surfaces on one side of said first and second light guides;
    first and second driving circuits outputting respectively first and second image signals photoelectrically converted by applying respectively first and second driving signals to said first and second solid state imaging devices;
    first and second video signal processing circuits processing respectively said first and second image signals to produce respectively standard first and second video signals;
    first and second monitors displaying respectively said first and second video signals; and
    a synchronization controlling means synchronizing the illuminating periods of the respective wavelength ranges of said first and second field sequential illuminating lights by said first and second light source apparatus.

2. An endoscope system according to claim 1 wherein said first electronic endoscope has a channel through which a treating instrument is to be passed and said second electronic endoscope has an insertable section of a small diameter which can be passed through said channel.

3. An endoscope system according to claim 1 wherein, in said first driving circuit, a synchronizing signal is applied from said synchronization controlling means and the timing of said first driving signal is controlled by said synchronizing signal.

4. An endoscope system according to claim 1 wherein, in said second driving circuit, a synchronizing signal is applied from said synchronization controlling means and the timing of said second driving signal is controlled by said synchronizing signal.

5. An endoscope system according to claim 1 wherein, in said second driving circuit, the timing of said second driving signal is controlled by the output of a means for detecting means of the illuminating period of said second field sequential illuminating light by said second light source apparatus.

6. An endoscope system according to claim 1 wherein, in said first light source apparatus, when a rotary filter fitted in the peripheral direction with a plurality of filters respectively different in the wavelength range to be passed is rotated and driven by a motor for the light generated from a lamp, said first field sequential illuminating light will be emitted through the filter in the position opposed to said lamp.

7. An endoscope system according to claim 1 wherein, in said second light source apparatus, when a rotary filter fitted in the peripheral direction with a plurality of filters respectively different in the wavelength range to be passed is rotated and driven by a motor for the light generated from a lamp, said second field sequential illuminating light will be emitted through the filter in the position opposed to said lamp.

8. An endoscope system according to claim 6 wherein said first light source apparatus has a means for detecting the emitting period of said first field sequential illuminating light, has a PLL circuit for synchronizing the output of said detecting means and the synchronizing signal output from said synchronization controlling means and the rotation of said motor is controlled by the output of said PLL circuit.

9. An endoscope system according to claim 7 wherein said second light source apparatus has a means for detecting the emitting period of said first field sequential illuminating light, has a PLL circuit for synchronizing the output of said detecting means and the synchronizing signal output from said synchronization controlling means and the rotation of said motor is controlled by the output of said PLL circuit.

10. An endoscope system according to claim 1 wherein said synchronization controlling means feeds a synchronizing signal to said first video signal processing circuit to process a signal synchronized with said synchronizing signal.

11. An endoscope system according to claim 1 wherein said synchronization controlling means feeds a synchronizing signal to said second video signal processing circuit to process a signal synchronized with said synchronizing signal.

12. An endoscope system according to claim 1 wherein said synchronization controlling means is provided in a first camera controlling unit, housing said first driving circuit and said first video signal processing circuit.

13. An endoscope system according to claim 1 wherein said second driving circuit and said second video signal processing circuit have a synchronizing circuit provided within the second camera controlling unit, synchronized with a synchronizing signal output from said synchronization controlling means and controlling said second driving circuit and said second video signal processing circuit.

14. An endoscope system according to claim 13 wherein said second camera controlling unit further has a synchronizing signal generating means and a switching means selecting the synchronizing signal outut from said synchronizing signal generating means and the synchronizing signal output from said synchronization controlling means and inputting them into said synchronizing circuit.

* * * * *